United States Patent [19]
Wilson

[11] Patent Number: 5,509,530
[45] Date of Patent: Apr. 23, 1996

[54] COMPARTMENTALIZED DENTAL AMALGAM MIXING CAPSULE

[75] Inventor: Michael S. Wilson, Minden, Nev.

[73] Assignee: Wykle Research, Inc., Carson City, Nev.

[21] Appl. No.: 504,575

[22] Filed: Jul. 20, 1995

[51] Int. Cl.⁶ .............................. B65D 25/08; B65D 81/32
[52] U.S. Cl. .................... 206/220; 206/63.5; 206/222; 220/300
[58] Field of Search .................... 206/63.5, 219–222, 206/459.1; 220/293, 300

[56] References Cited

U.S. PATENT DOCUMENTS

| | | |
|---|---|---|
| 3,425,598 | 2/1969 | Kobernick ............................ 206/222 |
| 3,638,918 | 2/1972 | Denholtz . |
| 3,831,742 | 8/1974 | Gardella et al. . |
| 3,841,467 | 10/1974 | Hansen . |
| 3,860,114 | 1/1975 | Merckardt . |
| 3,917,062 | 11/1975 | Winters . |
| 3,963,120 | 6/1976 | Perfect . |
| 4,142,629 | 3/1979 | Biondo et al. . |
| 4,197,943 | 4/1980 | Weikel . |
| 4,306,651 | 12/1981 | Muhlbauer . |
| 4,449,645 | 5/1984 | Korwin et al. . |
| 4,450,958 | 5/1984 | Prasad . |
| 4,470,505 | 9/1984 | Korwin et al. . |
| 4,515,267 | 5/1985 | Welsch . |
| 4,557,376 | 12/1985 | Probst et al. . |
| 4,863,017 | 9/1989 | Vlock . |
| 5,088,830 | 2/1992 | Muhlbauer . |
| 5,217,114 | 6/1993 | Gadberry et al. ............... 220/300 |
| 5,394,980 | 3/1995 | Tsai . |
| 5,396,986 | 3/1995 | Fountain et al. . |

Primary Examiner—Jimmy G. Foster
Attorney, Agent, or Firm—Fulwider Patton Lee & Utecht

[57] ABSTRACT

A compartmentalized dental amalgam mixing capsule including an upstanding elongated receptacle having a cylindrical interior chamber for receipt of an alloy therein. The receptacle is formed with an annular flange in the upper portion of the chamber including a central opening and formed with at least one lock pin projecting laterally outwardly from the receptacle. A rupturable pillow containing mercury therein is configured to overlie the flange. An elongated cylindrical cap formed with a closed top end, an open bottom end, and includes a piston device carried from the top end projecting axially downwardly therefrom to terminate in a hammer end configured to overlie the pillow. The cap is further formed with an elongated groove slidably receiving the lock pin and angling axially upwardly in one circumferential direction. The cap is telescopically received over the open end of the receptacle so that rotation of the cap in the direction opposite the one direction will draw the cap axially from a first position to a second position. As the cap is rotated, it is shifted from the first to the second position to drive the hammer end thereof downwardly toward the flange a distance sufficient to rupture the pillow and introduce the mercury through the central opening in the flange into the chamber for mixing with the alloy.

16 Claims, 2 Drawing Sheets

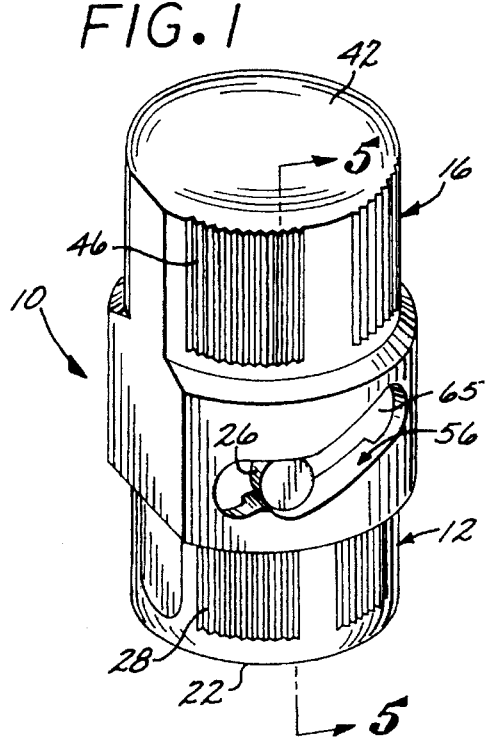
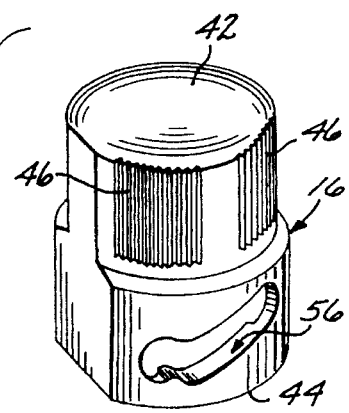
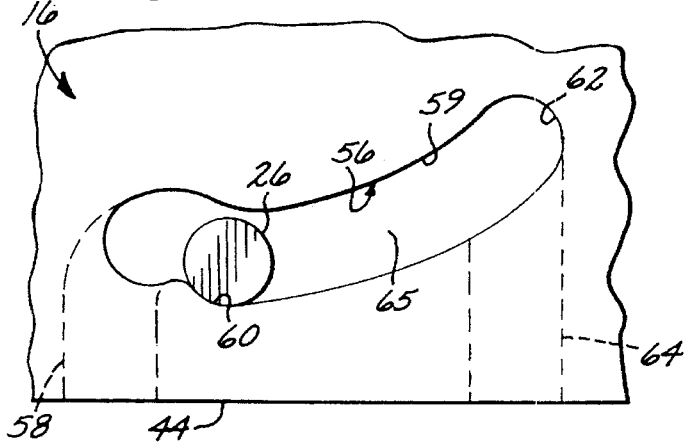
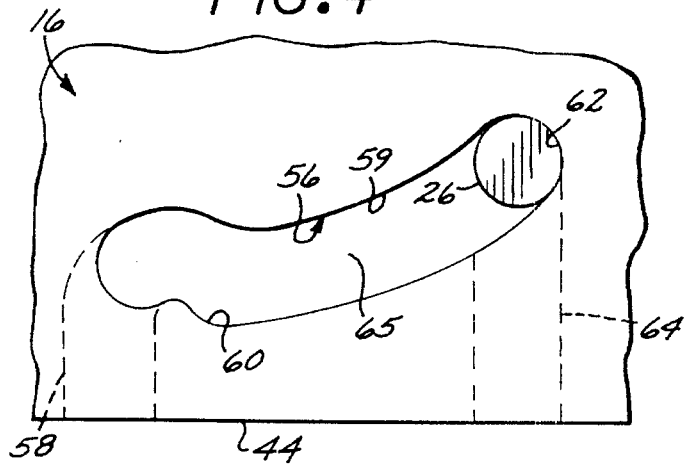
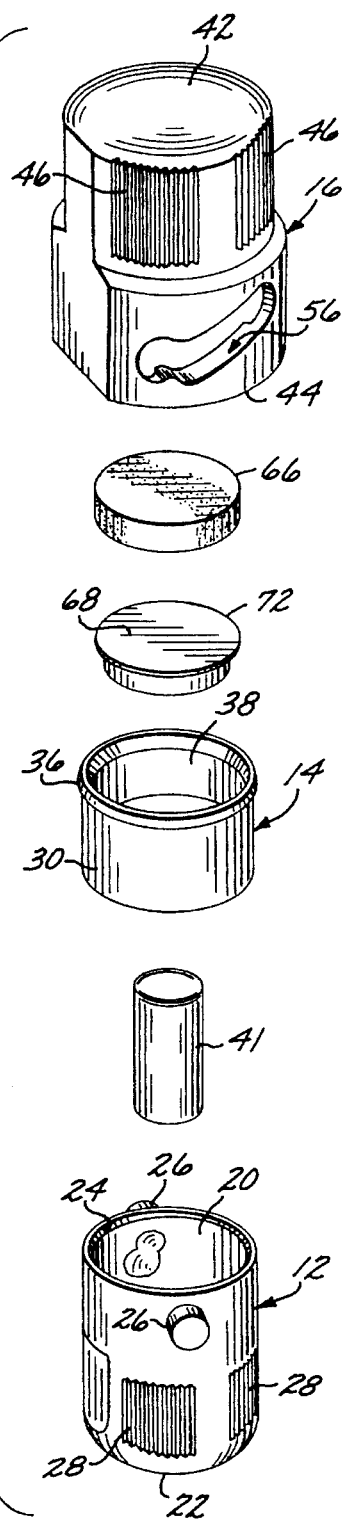

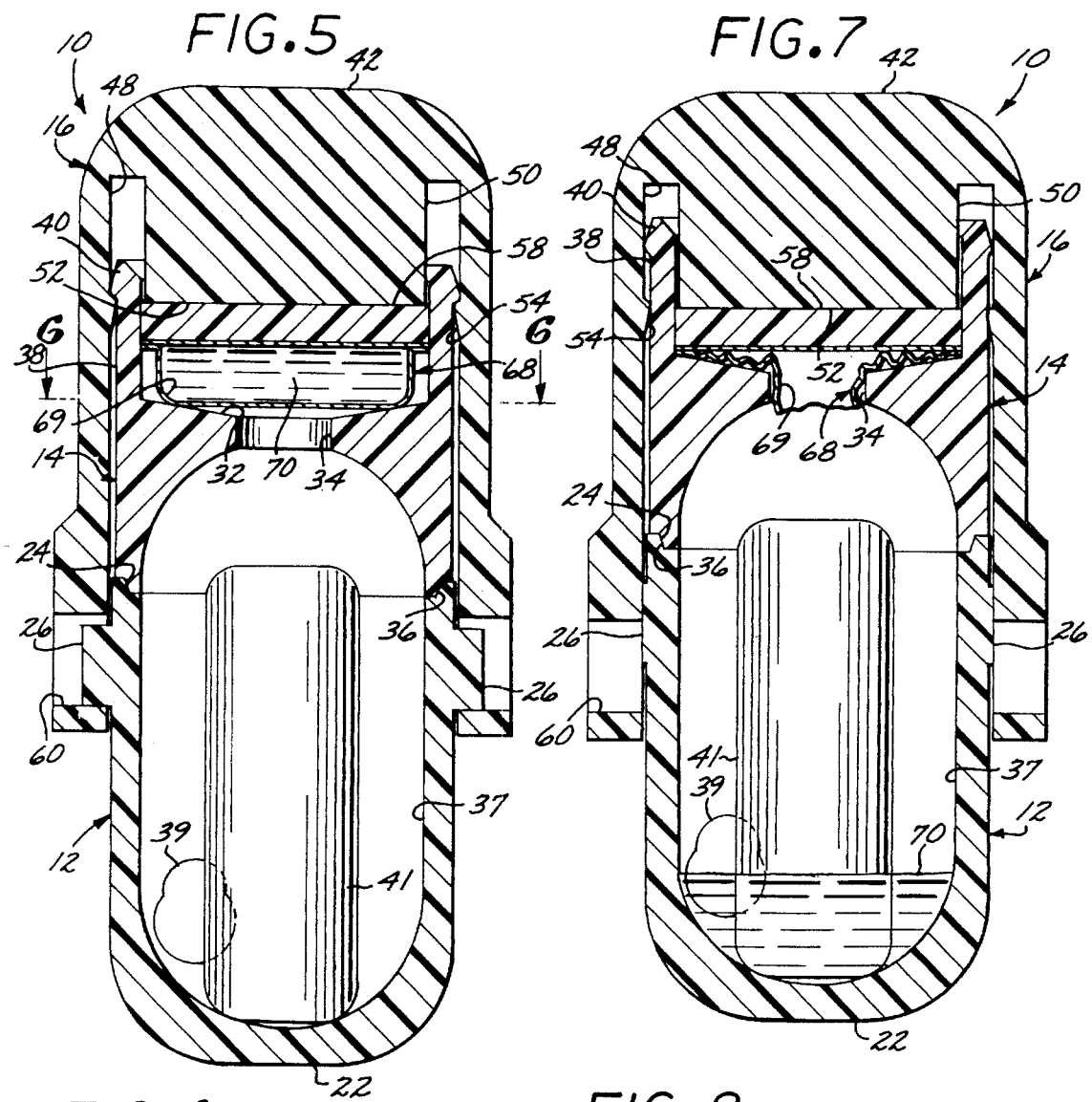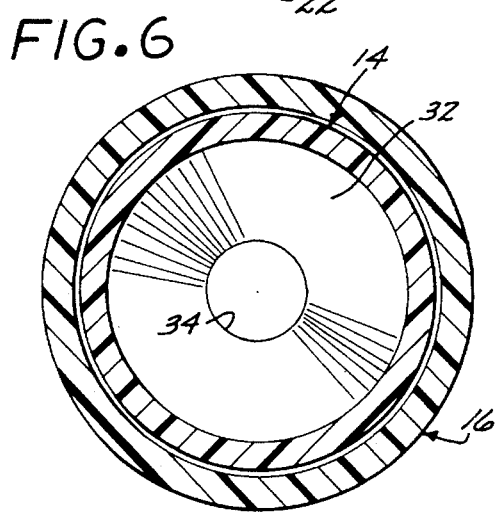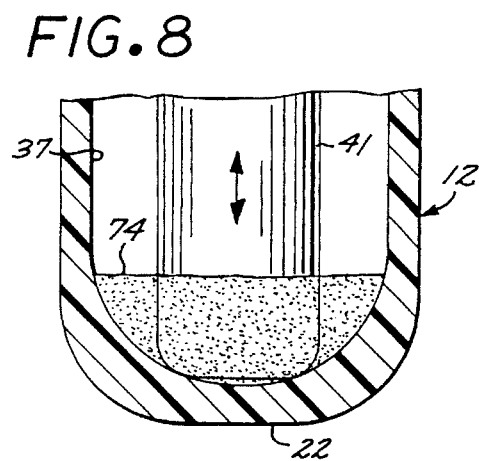

COMPARTMENTALIZED DENTAL AMALGAM MIXING CAPSULE

BACKGROUND OF THE INVENTION

1. Field of the Invention

The present invention relates to a compact device for containing and storing a plurality of chemicals and, more particularly to a device for containing such chemicals partitioned from one another, while in addition providing a means for conveniently mixing such chemicals into a composition for use.

2. Description of the Prior Art

Dental amalgams are commonly used to fill cavities drilled in teeth. An amalgam is formed by mixing a powdered or pelletized alloy with a small quantity of liquid mercury. The alloy is usually composed of a precious metal such as silver or gold combined with copper, zinc and tin. When the alloy and mercury are mixed they initially form a pliable amalgam that may be introduced into the cavity of the tooth where the dentist has drilled to remove decayed material. Once deposited in the cavity, the amalgam hardens very quickly to form a hard durable filling.

Others have provided the mercury and alloy in predetermined quantities housed in capsule form to provide a typical dosage of amalgam. The predetermined quantities of alloy and mercury must be separated so that premature mixing does not occur and the amalgam prematurely hardened. As such, the capsule is usually formed by a mixing chamber containing the alloy therein, and a second chamber containing the mercury, the two chambers separated by a partition or separating wall. When it is desired to mix the amalgam, the separating wall is removed or otherwise penetrated to allow the mercury to enter the mixing chamber. The capsule is then mechanically or manually shaken to mix the amalgam in the mixing chamber. The capsule may be opened to access the amalgam for subsequent application into the cavity of the tooth.

One particular mixing capsule is disclosed in U.S. Pat. No. 3,841,467. This capsule includes a cylindrical container closed at its bottom end and open on its opposite end for receipt of alloy powder therein. A circular plug is configured to rest on the circular upper edge of the container and has a central opening therethrough. A sealed plastic pouch filled with mercury is placed between the upper surface of the plug and the inner top surface of a cylindrical hollow cap which is in close fit sliding engagement with the outer surface of the cylindrical container. Upon pressing the cap telescopically in an axial direction over the container and relative to the plug, the pouch is compressed between the cap and the plug with enough force to rupture the pouch to flow mercury through the central opening and into the container for mixing with the alloy contained in the container. Although the capsule of this construction may have proven effective in use, the close fit slidable engagement between the cap and the container may not provide sufficient positive engagement therebetween to ensure that during shipment and storage the cap is not axially shifted or accidentally pressed downwardly upon the container to rupture the pouch causing premature mixing of the amalgam.

Others have provided threaded caps that may be threadedly engaged to the container for providing sufficient positive engagement therebetween to prevent accidental shifting of the cap relative to the container. Such threaded type of connection requires the clinician to rotate the cap a number of turns to provide sufficient axial displacement of the cap relative to the container to rupture the pouch, and also requires the clinician, once the amalgam has been mixed, to threadedly disengage the cap from the container to access the mixed amalgam contained therein. Although threaded connections may be utilized, it has been found desirable to provide a means for more easily and quickly displace the cap relative to the container for mixing, and then to more easily and quickly remove the cap from such container to access the mixed amalgam.

In addition, mixing capsules of the type described above do not typically provide any indicator for indicating when the cap has been either intentionally or accidentally shifted to cause the pouch to be ruptured.

Hence, those skilled in the art have recognized the need for a compact device to contain and store the components of a dental amalgam in a separated configuration therein and for conveniently mixing such components when desired to formulate an amalgam. It has been found desirable that such a mixing capsule facilitate quick and easy operation to combine such amalgam components for ease in mixing, and facilitate ease in accessing such amalgam once mixed. In addition, such a device should provide an indicator that allows the clinician to visualize whether or not the device is in an operative position for mixing the amalgam. Furthermore, it is desirable that such device incorporate a minimum number of relatively inexpensive components and be of a construction to facilitate ease of assembly. The present invention meets these needs and others.

SUMMARY OF THE INVENTION

The invention provides a compartmentalized dental amalgam mixing capsule for conveniently storing the components of the dental amalgam in a separated configuration and, when desired, for conveniently mixing such components to formulate the amalgam.

Briefly, and in general terms, the dental amalgam mixing capsule includes a receptacle formed with a cylindrical interior chamber for containing a predetermined amount of alloy, a rupturable pillow containing a predetermined amount of mercury, and a cap to overlie the pillow and the receptacle. The chamber is formed with an open top end and a closed bottom end and includes an annular flange in the upper portion of the chamber formed with a central opening therethrough. The rupturable pillow is of a predetermined length configured to be overlaid on the flange. The cap is generally cylindrical and is formed with a closed top end and an open bottom end formed with a piston carried from the top end and projecting axially downwardly therefrom to terminate in a hammer end. The cap is telescopically received over the open top end of the receptacle such that the hammer end of the piston overlies the pillow.

In addition, the receptacle is formed with laterally outwardly projecting lock pins and the cap is formed with complementally shaped elongated grooves angling axially away in one circumferential direction and slidably receiving the respective lock pins. Upon rotation of the cap in the direction opposite the one direction, the cap is drawn axially from a first position to a second position to drive the hammer end downwardly toward the flange a distance sufficient to rupture the pillow. As such, the mercury contained in the pillow flows through the central opening of the flange to intermix with the alloy in the chamber.

More particularly, the cap is formed with a pair of diametrically opposed elongated grooves angling axially upwardly in the one circumferential direction and the receptacle is formed with a pair of diametrically opposed outwardly projecting locking pins for slidable receipt within the respective pair of grooves.

In one aspect of the invention, the receptacle is formed with an upstanding outer wall having an indicator disposed thereon and the cap is formed with an opaque cylindrical outer wall with the grooves formed to open diametrically outward to define respective indicator windows. When the cap is telescopically received over the open top end of the receptacle, the indicator is aligned for visual indication through the window such that as the cap is shifted from the first to the second position, the indicator is displaced relative to the window to indicate the second position.

In a more particular aspect of the invention, a cylindrical plunger is provided for overlying the top end of the receptacle and is formed with the annular flange. The plunger is colored to define the indicator, such that the indicator is visible through the window when the cap is in the first position and is displaced axially from the window when the cap is in the second position.

In a further aspect of the invention, a spacer is provided and is interposed between the hammer end and the pillow such that when the cap is shifted from the first position to the second position, the hammer drives the spacer downward atop the pillow toward the flange a distance sufficient to rupture the pillow.

In another aspect of the invention, the cap is formed with an axially aligned downwardly opening annular channel and the plunger is formed with a tubular sleeve extending axially upwardly from the outer periphery of the annular flange and configured for slidable receipt within such channel. The channel defines therebetween the piston and is formed on its outer circumferential bottom end with a radially inwardly projecting annular retaining lip. In addition, the sleeve of the plunger is formed on its upper end with an outwardly flared annular abutment rim for, when the sleeve is received in the channel, abutting the retaining lip to hold the plunger on the cap.

In yet further aspects of the invention, the annular flange tapers inwardly and downwardly toward the central opening. In addition, a pestle is received in the chamber to facilitate improved mixing of the alloy and mercury in the chamber. Furthermore, the receptacle and the cap may be each integrally formed of thermoplastic material to lower manufacturing costs.

Other features and advantages of the invention will become apparent from the following detailed description taken in conjunction with the accompanying drawings, which illustrate by way of example, the features of the invention.

BRIEF DESCRIPTION OF THE DRAWINGS

FIG. 1 is a perspective view of a compartmentalized dental amalgam mixing capsule embodying the present invention;

FIG. 2 is a reduced-in-scale, exploded perspective view, of the compartmentalized amalgam mixing capsule shown in FIG. 1;

FIG. 3 is an enlarged fragmented side view of the compartmentalized amalgam mixing capsule shown in FIG. 1;

FIG. 4 is an enlarged side view, similar to that shown in FIG. 3;

FIG. 5 is an enlarged cross sectional view of the mixing capsule taken along line 5—5 of FIG. 1, and illustrating the mixing capsule in a first stored position;

FIG. 6 is a cross sectional view taken along line 6—6 of FIG. 5;

FIG. 7 is a cross sectional view similar to FIG. 5, but illustrating the mixing capsule in a second mixing position; and FIG. 8 is a fragmented side view of the mixing capsule shown in FIG. 7 containing the mixed amalgam.

DETAILED DESCRIPTION OF THE PREFERRED EMBODIMENT

As shown in the drawings for purposes of illustration, the invention is embodied in a compartmentalized dental amalgam mixing capsule for storing, in partitioned fashion, the components of a dental amalgam components and, when desired, for mixing such components therein to form such dental amalgam.

The compartmentalized mixing capsule of the invention provides a straight forward, reliable storage and mixing device that may be easily assembled and incorporating a minimum number of components formed of relatively inexpensive thermoplastic materials so that manufacturing costs are held to a minimum. In addition, the construction of the amalgam mixing capsule facilitates ease in operation for combining and mixing the components of the amalgam to quickly formulate the dental amalgam. In addition, the construction facilitates quick and easy access to the mixed amalgam for subsequent application within an evacuated cavity of a patient's tooth. Furthermore, the mixing capsule provides an indicator which allows the dental clinician to visually determine when the mixing capsule has been disposed in its mixing position.

Referring to the drawings and, in accordance with the invention, the compartmentalized amalgam mixing capsule 10 is of cylindrical construction and, in general, includes a cylindrical receptacle 12, a concentric plunger 14 to overlie the receptacle, and a cylindrical cap 16 for telescopical receipt over such plunger and the top end of such receptacle.

The receptacle 12, plunger 14 and cap 16 may be composed of a polymeric or thermoplastic material, such as polyvinyl chloride (PVC), which provides sufficient rigidity and structural integrity to the amalgam mixing capsule 10 while minimizing production and manufacturing costs. The aforementioned components may be formed using injection molding techniques well known to those skilled in the art. In addition, such materials have been selected to be chemically compatible with the chemical components of the amalgam to be stored and mixed in the capsule.

As shown in FIGS. 2, 5 and 7, receptacle 12 is generally cylindrical having a tubular outer wall 18 formed with an open top end 20 and a closed bottom end 22, the interior bottom surface thereof being hemispherically concave. With particular reference to FIGS. 5 and 7, the top end of the tubular outer wall is formed with a slight counterbore to define a radially inwardly and downwardly angled annular taper defining a seat 24. In addition, the outer wall of the receptacle is formed with a pair of radially outwardly projecting, diametrically opposed cylindrical locking pins 26 spaced a predetermined distance from the top extremity of the receptacle. As shown in FIGS. 1 and 2, the bottom end of the receptacle may be formed with a rough outer surface, formed for instance by knurling 28, to provide a positive gripping surface for a clinician's fingers when the mixing capsule is in use.

The plunger 14 is generally in the form of a hollow cylindrical tube having a peripheral wall 30 and formed intermedially with a transverse flange 32 extending radially inwardly from such peripheral wall and formed with an axial central opening 34 therethrough. The top surface of the flange tapers slightly downwardly and radially inwardly from its outer periphery to the central opening. The bottom surface of the flange is generally concave opening downwardly and is hemispherical in form. The bottom extremity of the plunger wall is formed with an annular lip 36 tapering radially inwardly and downwardly for complementary engagement with the seat 24 of the receptacle 12. The top tubular portion of the plunger, above the flange 32, defines a sleeve 38 and is formed with a radially outwardly flared abutment rim 40 for holding the plunger onto the cap 16, described in more detail below. In addition, the plunger may be colored, for example red, to define an actuation indicator, the function and operation of which will also be described below.

As shown in FIGS. 5 and 7, the plunger is configured to be overlaid upon the receptacle, such that the interior volume of the receptacle and the bottom hemispherical surface of the plunger define therebetween a mixing chamber 37. The mixing chamber is sized to contain a predetermined volume of alloy 39 therein. The alloy may be composed of a precious metal such as silver or gold combined with copper, zinc and tin. As shown, the alloy is in the form of a solid mass, however, may be alternatively in powder form. It is to be appreciated that the plunger 14 and receptacle 12 may be integrally formed in one piece.

In addition, a generally elongated cylindrical pestle 41 is received in the mixing chamber 37 to facilitate improved mixing of the amalgam in the chamber. The pestle may be formed of stainless steel having a diameter and length sized for loose receipt within the mixing chamber.

As shown in FIG. 2, the cap 16 is generally elongated and cylindrical formed with a closed top end 42 and an open bottom end 44 configured for telescopical receipt over the receptacle 12 and the plunger 14. The outer wall of the cap steps intermedially in the downward direction to an enlarged-in-diameter portion being truncated longitudinally at diametrical opposite sides thereof. The upper portion of the cap may be formed with a rough outer surface, formed for instance by knurling 46, to provide a positive gripping surface for the clinician's fingers when the mixing capsule is in use.

With reference to FIGS. 5 and 7, the top end 42 of the cap 16 includes an annular, downwardly opening, coaxially aligned channel 48 sized for receipt of the sleeve 38 of the plunger 14. The annular channel defines a central piston or stub rod 50 carried from the top end of the cap projecting axially downwardly therefrom to terminate in a generally flat smooth surface to define a hammer or stub end 52. Radially outward from the plane of the stub end of the rod, the outer circumferential wall of the channel is formed with a radial inwardly projecting annular tapered retainer lip 54 for abutting the abutment rim 40 of the plunger 14 for holding the plunger 14 onto the cap when assembled as described below.

With particular reference to FIGS. 3 and 4, the cap 16 is formed with a pair of bayonet grooves (only one shown), generally indicated at 56, disposed at the diametrical opposite sides of such cap and configured for slidable receipt of the respective pair of locking pins 26 of the receptacle 12. At one end, the respective grooves are formed vertically upwardly from the bottom open end 44 of the cap 16 and are partially recessed from the inner surface of the wall of the cap to define an entrance slot 58, shown in phantom. From the entrance slot, the respective grooves are formed completely through the wall of the cap curving arcuately upwardly and then downwardly in one circumferential direction transitioning to a helical portion 59 angling in the axial direction upwardly in such circumferential direction to terminate at their respective opposite ends to define respective actuation seats 62. The transition portion from the downwardly curved portion of the groove and the first end of the helical portion 59 of the groove defines an intermediate locking or nesting seat 60, the function of which to be described below. From the actuation seat 62, the respective grooves extend vertically downwardly being partially recessed from the inner surface of the wall of the cap to terminate at the bottom end of the cap to define an exit slot 64, shown in phantom. It is to be appreciated that the respective locking pins 26 are configured to follow the path of the helical portions 59 of the respective grooves 56 as the cap 16 is operatively rotated relative to the receptacle, described below in more detail. The respective helical portions 59 are of a length selected to confine the locking pins 26 therein such that the cap 16 is restricted to 90 degrees of rotation relative to the receptacle 12 or otherwise one-quarter turn.

The respective helical through slotted portions 59 of the respective grooves 56 also define a respective pair of open windows 65, such that when the cap 16 and receptacle 12 are assembled, the clinician may view the colored plunger through such window to obtain a convenient indication of whether or not the mixing capsule 10 has been placed in its operative mixing position, described more fully below.

As shown in FIG. 2, piston device includes a spacer 66 interposed between the stub rod end 52 and a rupturable pillow 68 constrained within the tubular sleeve 38 of the plunger 14. As shown in FIGS. 5 and 7, with the cap 16 telescopically received over the open top end of the receptacle 14, the spacer 66 and pillow 68 are interposed between the stub rod end 52 of the rod 50 and the upper tapered surface of the plunger flange 32. More particularly, the rod end 52 of the rod 50 overlies the spacer 66, in turn overlying the pillow 68 such that the bottom end of the pillow engages the upper surface of the flange 32.

The spacer 66 is generally in the form of a flat cylindrical disk having an outer diameter sized for slidable receipt within the sleeve 38 of the plunger 14 and having predetermined axial dimension. The spacer 66 is formed of a resilient compressible material such as PVC foam.

The rupturable pillow 68 is hollow and generally in the form of a disk formed of a thin hollow rupturable peripheral casing 69 containing therein a predetermined volume of mercury 70. The pillow is of a predetermined axial dimension and is formed on the top end thereof with a radially outwardly extending flange 72 having an outer diameter sized for slidable receipt within the sleeve 38 of the plunger 14.

With particular reference to FIGS. 2 and 5, the assembly of the compartmentalized dental amalgam mixing capsule 10 will be described hereinafter. To assemble the mixing capsule 10, the assembler may first retrieve a plunger 14, a rupturable pillow 68 and a spacer 66 from inventory. With the sleeve 38 of the plunger 14 in an upwardly facing orientation as shown in FIG. 2, the pillow 68, with the pillow flange 72 thereof facing upwardly, may be introduced between the tubular wall of the sleeve 38 to overlie the upper surface of the plunger flange 32 and the central opening 34 thereof. The spacer 66 may then be received in the sleeve to overlie top surface of the pillow 68. Thereafter, the assembler may select a cap 16 and an orient the cap in the downwardly opening manner as shown to align the channel 48 thereof over the sleeve 38 of the plunger 14 while aligning the stub rod 50 over the spacer 66 and pillow 68. The plunger may be inserted upwardly within the open end of the cap to press the abutment rim 40 of the plunger sleeve 38 past the radial inwardly projecting retainer lip 54 of the channel 48 in snapping relationship to snap the plunger 14 and cap 16 together while sandwiching the spacer 66 and pillow 68 between the flange 32 of the plunger and stub end 52 of the rod 50 of the cap 16. It is to be appreciated that the spacer 66 applies a mild compressive force to the pillow, but being insufficient to rupture such pillow.

The assembler may then select a receptacle 12 and place the predetermined amount of alloy 39 therein followed by the pestle 41. Referring to FIGS. 3 and 4, with the receptacle in its upstanding orientation, the cap 16 and plunger 14 may be overlaid upon the receptacle to align the respective entrance slots 58 of the respective groove 56 with the respective outwardly projecting locking pins 26 of the receptacle 12. The cap 16 may be urged downwardly in telescopical relationship over the receptacle 12 to receive the respective pins 26 upwardly within the respective entrance slots 58 such that the annular lip 36, at the bottom end of the plunger 14, and the seat 24, at the top end of the receptacle 12, are engaged in complementary confronting relationship. In this position, the plunger 14 encloses the open end of the receptacle to encapsulate the alloy 39 and the pestle 41 within the mixing chamber 37. The cap 16 may then be rotated in the clockwise direction, viewed downwardly on the cap, relative to the receptacle 12 such that the respective locking pins 26 follow the respective upwardly and downwardly curving arcuate paths of the grooves 56 such that the locking pins nest in the respective nesting seats 60.

In this position, the cap 16 and receptacle 12 are disposed in the normal or first position. In this first position, it is to be appreciated that the resilient spacer 66 applies a slight expansive biasing force between the cap 16 and the receptacle 12 tending to separate the cap relative to the receptacle, and thus the respective locking pins 26 are urged in the downward direction relative the cap such that the respective pins remain nested in the respective nesting seats 60 to hold the cap in the first position relative to the receptacle. As such, the cap and receptacle are thus maintained in a position wherein the respective alloy 41 and mercury-filled pillow 58 are separated from one another.

It is to be appreciated that the snap assembly design of the plunger sleeve 36 in the channel 48 of the cap 16 as well as the interlocking groove 56 and pin 26 design of the cap 16 and receptacle 12 facilitate easy and convenient assembly of the mixing capsule 10 for completion of the assembly in a minimal amount of time and within a minimum number of steps.

Once assembled, the mixing capsule 10 may be packaged, for instance, in a protective plastic cover for storage. In addition, the packaged mixing capsule may be inserted in a box or the like to further protect the capsule from damage or tampering and to facilitate shipping and handling. As such, the amalgam mixing capsule 10 may be stored in the clinician's office for convenient and rapid retrieval for immediate use.

Referring now to FIGS. 5 and 7, operation of the mixing capsule 10 to mix the dental amalgam will be described hereafter in detail. To mix the dental amalgam, the clinician may remove the mixing capsule 10 from the packaging and securely grasp the knurling 46 of the cap 16 between his or her fingers in one hand and then grasp the knurling 28 of the receptacle 12 between the fingers of the other hand. The clinician may then conveniently rotate the cap in one direction, clockwise looking downwardly upon the top end of the cap, one quarter turn relative to the receptacle to cause the respective locking pins 26 to move from the respective nesting seats 60 (FIG. 3) to follow the helical portion 59 of the respective grooves 56 in camming relationship to drive the cap downwardly from its first position relative to the plunger 14 and receptacle 12 to nest the respective locking pins 26 in the actuation seat 62 at the opposite end of the helical groove (FIG. 4). As such, the cap is moved from its first position relative to the receptacle to a second or mixing position. As the cap 16 is driven downwardly relative to the receptacle 12, the stub rod 50 of such cap is driven downwardly within the sleeve 38 of the plunger 14 toward the flange 32 thereof to displace the spacer 66 downwardly compressing the pillow 58 between the upper surface of such flange 32 and such spacer 66 with sufficient force to rupture the casing 69 over the central opening 34 of such flange. Simultaneously as the rod 50 moves downwardly within the tubular sleeve 38, such sleeve 38 moves upwardly in guiding relationship within, and relative to, the annular channel 48 of the cap 16.

As shown in FIG. 7, it is to be appreciated that as the cap 16 is displaced from its first position to its second position, the stub end 52 of the rod 50 and the spacer 66, in controlled fashion, gradually collapse the casing 69 of the pillow to squeeze the mercury 70 contained therein downwardly through the central opening 34 in the plunger flange 32. The spacer is driven downwardly within the sleeve 38 of the plunger 14 substantially to the upper surface of the flange 32. In addition, it is to be appreciated that the tapered upper surface of the flange serves to direct the flow of mercury 70 inwardly to the central opening and into the mixing chamber 37. As mercury is introduced into the mixing chamber, it will flow downwardly around the pestle 41 to make fluid contact with the alloy 39 at the bottom of such chamber.

When the cap 16 is in its normal or first position on the receptacle 12, the colored plunger 14 is in clear view diametrically inwardly through the window 65 of the cap 16 to indicate that the mixing capsule 10 is in such first position. As the cap is displaced from its first position to the mixing or second position, it is to be appreciated that the colored plunger 14 moves vertically upwardly relative to the cap 16 and the window 65 thereof. As such, the plunger 14 may move partially or even entirely out of view from the window 65 to indicate that the mixing capsule 10 has been operatively positioned in its mixing position. This feature also provides the clinician with the ability to determine by simply viewing the capsule whether or not the cap 16 has been accidentally or prematurely rotated over the receptacle 12 to its mixing position, therefore indicating that the mercury 70 has already been introduced into the mixing chamber 37 and prematurely in contact with the alloy 41. In addition, when the cap 16 has been intentionally rotated on the receptacle 12 in order to purposefully mix the amalgam, the clinician can determined by easily viewing the capsule that such cap has been fully rotated down on such receptacle to introduce the correct predetermined volume of mercury 70 into the mixing chamber 37, thus ensuring the clinician that the mercury 70 and alloy 41 can be mixed in the proper proportions and form a high quality amalgam.

It is to be appreciated that the indicator being comprised of a colored plunger 14 may be formed alternatively, for instance, by placing or otherwise forming graduations, indicia or the like on the surface of the plunger or outer surfaces of the receptacle 12 or cap 16 to indicate the relative displacement of the cap relative to the receptacle to give the clinician a visual indication that the cap has been displaced from the normal or first position to the mixing or second position.

With reference to FIG. 8, once the mercury 70 has been introduced into the mixing chamber 37, the clinician may place the mixing capsule 10 in a mechanical vibrating device or in the palm of one hand and place his or her thumb over the cap 16 and shake the capsule vigorously to mix the mercury 70 with the alloy 39. As such, the pestle 41 is vibrated in the mixing chamber 37 to facilitate thorough mixing of the mercury with the alloy to form the dental amalgam 74. It is to be appreciated that the mixing of the dental amalgam may be completed in a very short period of time, perhaps in only a matter of one or two minutes.

Because such amalgam 74 hardens very quickly, it is desirable that the clinician have easy and quick access to such amalgam for application within the cavity of the patient's tooth. To access such amalgam, the clinician may orient the mixing capsule 10 to its normal upright position with the cap 16 in the upward orientation and pull upwardly on such cap. As such, the respective locking pins 26 move vertically downwardly from the respective actuation seats 62 within the respective exit slots 64 (FIG. 4) to remove the cap 16 from the top end of the receptacle 12 such that the abutment rim 40 of the plunger 14 abuts the retaining lip 54 of the cap to carry the plunger 14 therewith. The pestle 41 may then be withdrawn from the receptacle to give access to the mixed dental amalgam 74 in the bottom of the mixing chamber 37.

From the foregoing it can be appreciated that the compartmentalized amalgam mixing capsule of the invention provides a compact device for storing the components of a dental amalgam in a separated configuration therein, and when desired, for conveniently mixing such components to formulate the dental amalgam. The mixing capsule facilitates quick and easy operation for combining and mixing such amalgam components, and facilitates easy access to such amalgam once mixed. In addition, the mixing capsule provides an indicator that allows the clinician to visualize whether or not the capsule has been placed in an operative position to mix the amalgam. Furthermore, the mixing capsule incorporates a minimum number of components formed of relatively inexpensive materials of a construction that facilitate ease of assembly to thereby minimize manufacturing and production costs.

While particular forms of the invention have been illustrated and described, it will be apparent that various modifications can be made without departing from the spirit and scope of the invention.

What is claimed is:

1. A compartmentalized dental amalgam mixing capsule comprising:

an upstanding elongated receptacle having a cylindrical interior chamber for receipt of an alloy therein and formed with a closed bottom end and an open top end and at least one lock pin projecting laterally outwardly from said outer wall;

an annular flange in the upper portion of said chamber and formed with a central communication opening;

a rupturable pillow of a predetermined length on said flange and containing mercury therein;

an elongated cylindrical cap formed with a closed top end and an open bottom end to be telescopically received over said open top end of said receptacle and formed with an elongated groove slidably receiving said lock pin and angling axially upwardly in one circumferential direction so that rotation of said cap in the direction opposite said one direction will draw said cap axially from a first position to a second position, said cap including a piston device carried from said top end and projecting axially downwardly therefrom to terminate in a hammer end to, when said cap is in said first position, overlie said pillow and as said cap is rotated to be shifted from said first to said second position, drive said hammer end downward toward said flange a distance sufficient to rupture said pillow.

2. A compartmentalized dental amalgam mixing capsule as set forth in claim 1 wherein:

said receptacle is formed with an upstanding outer wall having an indicator disposed thereon; and said cap is formed with a cylindrical outer wall wherein said groove is formed completely therethrough to define a window to be, when said cap is received over said open top end of said receptacle, aligned with said indicator for visual indication of said indicator therethrough, and to be, when said cap is shifted from said first to said second position, displaced relative said indicator to indicate said second position.

3. A compartmentalized dental amalgam mixing capsule as set forth in claim 2 wherein:

said receptacle includes a cylindrical plunger formed interiorly with said annular flange and configured for overlying the top end of said receptacle and wherein;

said plunger is configured to be visible through said window when said cap is in said first position and disposed axially out of alignment with said window when said cap is in said second position.

4. A compartmentalized dental amalgam mixing capsule as set forth in claim 1 wherein:

said piston device includes an elongated cylindrical stub rod carried from said top wall and formed with a stub end and a spacer of a selected axial length interposed between said stub end and said pillow to, when said cap is shifted from said first to said second position, drive said spacer downwardly toward said flange a distance sufficient to rupture said pillow.

5. A compartmentalized dental amalgam mixing capsule as set forth in claim 1 that includes:

a cylindrical pestle is received in said chamber.

6. A compartmentalized dental amalgam mixing capsule as set forth in claim 1 wherein:

said annular flange tapers inwardly and downwardly toward said opening.

7. A compartmentalized dental amalgam mixing capsule as set forth in claim 1 wherein:

said cap is formed with a peripheral cylindrical wall and configured with a concentric stub rod depending from said top wall and cooperating with said peripheral cylindrical wall to define a downwardly opening annular channel said cylindrical unit being configured with a radially inwardly projecting annular retaining rim; and said receptacle device includes a tubular sleeve extending axially upwardly from the outer periphery of said annular flange configured for slidable receipt within said annular channel and formed on its upper end with an outwardly flared annular retainer lip to, when said cap is in said first position, engage said retaining rim.

8. A compartmentalized dental amalgam mixing capsule as set forth in claim 1 wherein:

said receptacle and said cap are each integrally formed of thermoplastic material.

9. A compartmentalized dental amalgam mixing capsule comprising:

an elongated receptacle formed with a peripheral wall defining a cylindrical interior chamber for receipt of an alloy therein and formed with a closed bottom end, an open top end and at least one lock pin projecting laterally outwardly from said wall;

an indicator disposed on said outer wall;

an interior annular flange in the upper portion of said chamber and formed with a central opening;

a rupturable pillow of a predetermined axial length on said flange and containing mercury therein;

an elongated cylindrical cap formed with a closed top end and an open bottom end to be telescopically received over said open top end of said receptacle and axially movable from a first position to a second position, said cap being formed with a window configured to be aligned with said indicator for visual indication of said indicator therethrough, and said cap further including a piston device connected to said top end and projecting axially downwardly therefrom to terminate in a hammer end to, when said cap is in said first position, overlie said pillow, and as said cap is shifted from said first to said second position, drive said hammer surface downward toward said flange a distance sufficient to rupture said pillow and to displace said indicator relative said window to indicate said second position.

10. A compartmentalized dental amalgam mixing capsule as set forth in claim 9 wherein:

said cap is formed with a pair of diametrically opposed elongated grooves angling axially upwardly in one circumferential direction; and said receptacle is formed with a pair of diametrically opposed outwardly projecting locking pins slidably received in the respective said pair of grooves so that rotation of said cap in the direction opposite said one direction will draw said cap axially from said first position to a second position.

11. A compartmentalized dental amalgam mixing capsule as set forth in claim 9 wherein:

said piston device includes a stub rod carried from said top end and terminating at its bottom end spaced when said cap is in said first position, a predetermined distance from said pillow, and a spacer of a selected axial length corresponding with said predetermined distance and interposed between said rod surface and said pillow to, when said cap is rotated to be shifted from said first to said second position, drive said spacer downward toward said flange a distance sufficient to rupture said pillow.

12. A compartmentalized dental amalgam mixing capsule as set forth in claim 9 wherein:

a cylindrical pestle is received in said chamber.

13. A compartmentalized dental amalgam mixing capsule as set forth in claim 9 wherein:

the top surface of said annular flange tapers inwardly and downwardly toward said opening.

14. A compartmentalized dental amalgam mixing capsule as set forth in claim 9 wherein:

said receptacle includes a cylindrical plunger formed with said annular flange and configured for overlying the top end of said receptacle and wherein;

at least a portion of said plunger device is colored to define said indicator, said portion being visible through said window when said cap is in said first position and being invisible through said window when said cap is in said second position.

15. A compartmentalized dental amalgam mixing capsule as set forth in claim 9 wherein:

said cap is formed with a cylindrical peripheral wall and a concentric central stub piston rod cooperating with said peripheral wall to define an axially aligned downwardly opening annular channel configured on its bottom end with a radially inwardly projecting annular retaining rim; and said receptacle is formed with a tubular sleeve extending axially upwardly from the outer periphery of said annular flange configured for slidable receipt within said annular channel and formed on its upper end with an outwardly flared annular retainer lip to, when said cap is in said first position, engage said retaining rim.

16. A compartmentalized dental amalgam mixing capsule as set forth in claim 9 wherein:

said receptacle and said cap are each integrally formed of thermoplastic material.

* * * * *